United States Patent
Saarinen

(10) Patent No.: US 7,820,046 B2
(45) Date of Patent: Oct. 26, 2010

(54) FILTER ASSEMBLY FOR SAMPLING

(75) Inventor: Voitto Saarinen, Espoo (FI)

(73) Assignee: Outotec Oyj, Espoo (FI)

( * ) Notice: Subject to any disclaimer, the term of this patent is extended or adjusted under 35 U.S.C. 154(b) by 860 days.

(21) Appl. No.: 11/577,482

(22) PCT Filed: Oct. 26, 2005

(86) PCT No.: PCT/FI2005/000457

§ 371 (c)(1),
(2), (4) Date: Apr. 18, 2007

(87) PCT Pub. No.: WO2006/045883

PCT Pub. Date: May 4, 2006

(65) Prior Publication Data

US 2008/0035549 A1    Feb. 14, 2008

(30) Foreign Application Priority Data

Oct. 29, 2004    (FI) ................................. 20041399

(51) Int. Cl.
*B01D 35/22* (2006.01)
*B01D 29/19* (2006.01)
*B01D 63/06* (2006.01)

(52) U.S. Cl. .................... 210/304; 210/305; 210/306; 210/321.87; 210/321.9

(58) Field of Classification Search ................ 210/304, 210/305, 306, 321.87, 321.9
See application file for complete search history.

(56) References Cited

U.S. PATENT DOCUMENTS

| 280,828 | A | * | 7/1883 | Howes | ............ 210/412 |
|---|---|---|---|---|---|
| 2,198,819 | A | * | 4/1940 | Holm | ............ 210/304 |
| 3,754,658 | A |   | 8/1973 | Messing | |
| 4,243,536 | A |   | 1/1981 | Prolss | |
| 4,727,758 | A |   | 3/1988 | Murdock | |
| 5,602,348 | A |   | 2/1997 | Takakarhu et al. | |
| 5,628,909 | A | * | 5/1997 | Bellhouse | ............ 210/650 |
| 5,871,645 | A | * | 2/1999 | Reed et al. | ............ 210/493.2 |
| 5,916,443 | A | * | 6/1999 | Mueller et al. | ............ 210/346 |
| 6,155,430 | A | * | 12/2000 | Goodman | ............ 210/355 |

* cited by examiner

*Primary Examiner*—Thomas M Lithgow
(74) *Attorney, Agent, or Firm*—Chernoff, Vilhauer, McClung & Stenzel

(57) ABSTRACT

A filter assembly is provided for obtaining a filtered liquid sample from slurry, such as a liquid process stream that contains liquid, dissolved matter and solids. A housing defines a cavity. A rod is arranged in the cavity and supports a filter. A cartridge comprises the filter, and is arranged between the housing and the rod. Furthermore, there is a helicoidal passage for a slurry defined by the housing and the cartridge. There is also a cavity defined by the rod and the cartridge. The slurry has velocity that generates scouring and cleaning action on the filter media thus preventing cake formation on the filter. The filtering apparatus of the present invention provides reliable and continuous on-line sample delivery for an analyzer.

12 Claims, 5 Drawing Sheets

FILTER ASSEMBLY FOR SAMPLING

This is a national stage application filed under 35 USC 371 based on International Application No. PCT/FI2005/000457 filed Oct. 26, 2005, and claims priority under 35 USC 119 of Finnish Patent Application No. 20041399 filed Oct. 29, 2004.

The present invention is directed to the filed of solid-liquid separation by means of filtration. More specifically, the present invention concerns a method and apparatus for obtaining a filtered sample from a process stream that comprises liquid, dissolved matter and solids.

In industrial processes involving handling and processing of solids containing liquids, it is often necessary to control the process regularly and continuously. Several analyzing methods used to today can be performed only with liquids free of solids. Such methods are for example optical analyzing methods, conductivity measurements, pH measuring and methods utilizing x-rays such as x-ray fluorescence analysis. In order to monitor rapidly evolving industrial processes and control them optimally on the basis of the results of such measurements, it is necessary to take samples from a process stream continuously and analyze them instantaneously and without delay. Examples of industrial processes requiring real-time on-stream analyzing of liquids are processes in the field of hydrometallurgy. Leaching metals, liquid purification and electrolytic refining and recovering processes represents such hydrometallurgical processes where on-stream analyzers are used.

For the purpose of providing an on-line analyzer with a filtered flow of process liquor, several filtering apparatus have been developed. According to a known approach of removing solids from a liquid the principles of cross-flow filtration are utilized. The publication of a U.S. Pat. No. 3,674,153 discloses a cross-flow type filter, i.e. a bypass filter assembly for obtaining a filtered sample from a process stream. The filter assembly comprises a filter medium and a filter chamber involving a washing action property wherein the fluid passes the filter medium in a relatively high velocity and thus prevents cake deposition on the filter surface. However, in the filter assembly of U.S. Pat. No. 3,674,153, fast cake deposition still takes place and a need for frequently replacing the filter media with a fresh one exists.

SUMMARY OF THE INVENTION

The object of the present invention is to overcome the problems related to prior art and provide a novel apparatus for continuous sampling of an industrial process stream, such as liquid flow of a hydrometallurgical process. The filtering apparatus of the present invention continuously provides analyzer equipment with a solid-free sample of the process flow. The filtering apparatus produces a sample flow that represents real-time conditions of the process. The sample flow is formed when a liquid flow of an industrial process is fed into the inlet of an filtering apparatus and flows cross a filtering medium where part of the liquid passes through the filtering medium and enters the outlet of the filtering apparatus.

Another object of the invention is to provide a filtering apparatus with relatively long maintenance interval and with easy replacement of the filtering cartridge.

The filtering apparatus of the present invention has excellent washing action property that prevents cake deposition on the filter surface. Most of the feed into the filtering unit passes over the filter surface and exits the unit via an outlet port for the solid-containing flow. Only a minor part of the liquid in the feed passes through the filtering media. The liquid flow is fed into the fluid passageway of the filtering apparatus at a velocity sufficient to induce shear-cleansing current across the filter surface.

The filter cartridge contains filtering media that is flexible cloth that comprises textile or web, such as web comprising polypropylene or polyamide. The filtering media is chosen according to the type of the process slurry. The filter cartridge is arranged to the filter housing in a manner that provides easy maintenance of the filter, i.e. the filter cartridge is easy to remove and reinstall.

The filtering apparatus of the present invention provides reliable and continuous on-line sample delivery for an analyzer. The filtering apparatus may function continuously for several weeks.

The filtered sample created with the filtering apparatus of the present invention represents exactly the real-time composition of the process flow, since accumulation of the sample in the filtering apparatus is minimized with eliminating dead volume inside the filter cavity. This is accomplished by applying a filler rod inside the filter cavity and the filtering cartridge.

The present invention provides a filter assembly for obtaining a filtered liquid sample from slurry, such as liquid process stream that contains liquid, dissolved matter and solids. The process flow having kinetic energy is fed into a filter chamber so as to provide a helicoidal flow pattern of the slurry on a surface of a filter media. The slurry has velocity that generates scouring and cleaning action on the filter media thus preventing cake formation on the filter.

The filter assembly comprises an elongated cylindrical cartridge housing defining a filter cavity, a slurry feed port, a slurry outlet port and a filtrate outlet port, a solid filler rod that is arranged to eliminate dead volume of the filter cavity and to support flexible filtering media, a cylindrical filter cartridge comprising said flexible filtering media arranged between the inner surface of the housing and the solid filler rod, and a helicoidal passage way for the slurry defined by the inner surface of the housing and outer surface of the filter cartridge. The slurry feed port and the slurry outlet port are both in fluid communication with the helicoidal passage way, and the filtrate outlet port is in fluid communication with an annular cavity defined by the solid filler rod and inner surface of the cylindrical filter cartridge.

Time to time, the filtering media needs to be cleaned by backflushing action. The flexible filtering media promotes the cleaning action, since it bulges outwards form the surface of the filler rod, whereas during normal operation, the filtering media is pressed against the filler rod.

BRIEF DESCRIPTION OF THE DRAWINGS

The invention is described in more detail referring to following drawings, where.

DETAILED DESCRIPTION OF THE PREFERRED EMBODIMENTS

Figure 1:
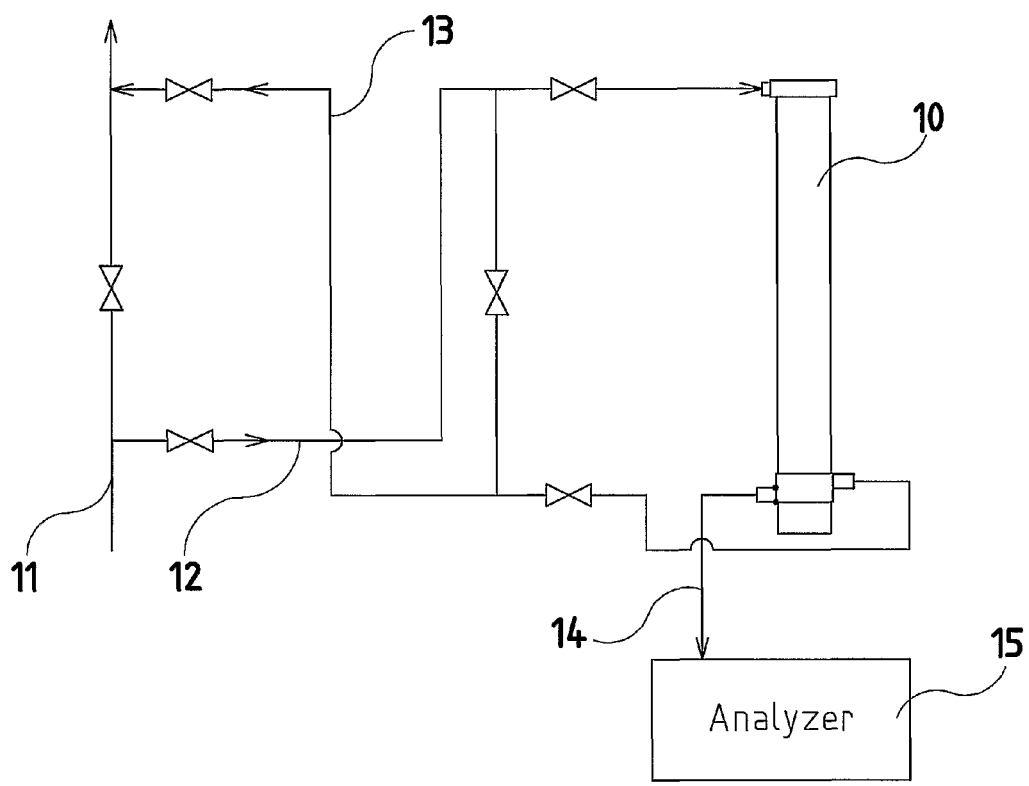
FIG. 1 shows a simplified flow chart of the filter assembly according to the present invention.

FIG. 1 shows a simplified chart of one possible coupling of the filtering assembly of the present invention between process flow and analyzer equipment. The filtering apparatus 10 is preferably operated in vertical position. Flow 12 is withdrawn from main process stream 11 and led to an inlet port arranged in the upper end of the filtering apparatus 10. Flow 13 passed through the spiral passageway of the filtering apparatus 10 and exited the slurry outlet port is returned to main process stream 11. Filtered sample flow 14 is forwarded to an analyzer apparatus 15. The filtering assembly provides the analyzer with a small quantity of filtered sample returning the bulk of the sample intake to the process. The analyzer equipment may comprise a pneumatic sample dispatch station for transporting the filtered sample to the analysis chamber of the analyzer.

Figure 2:
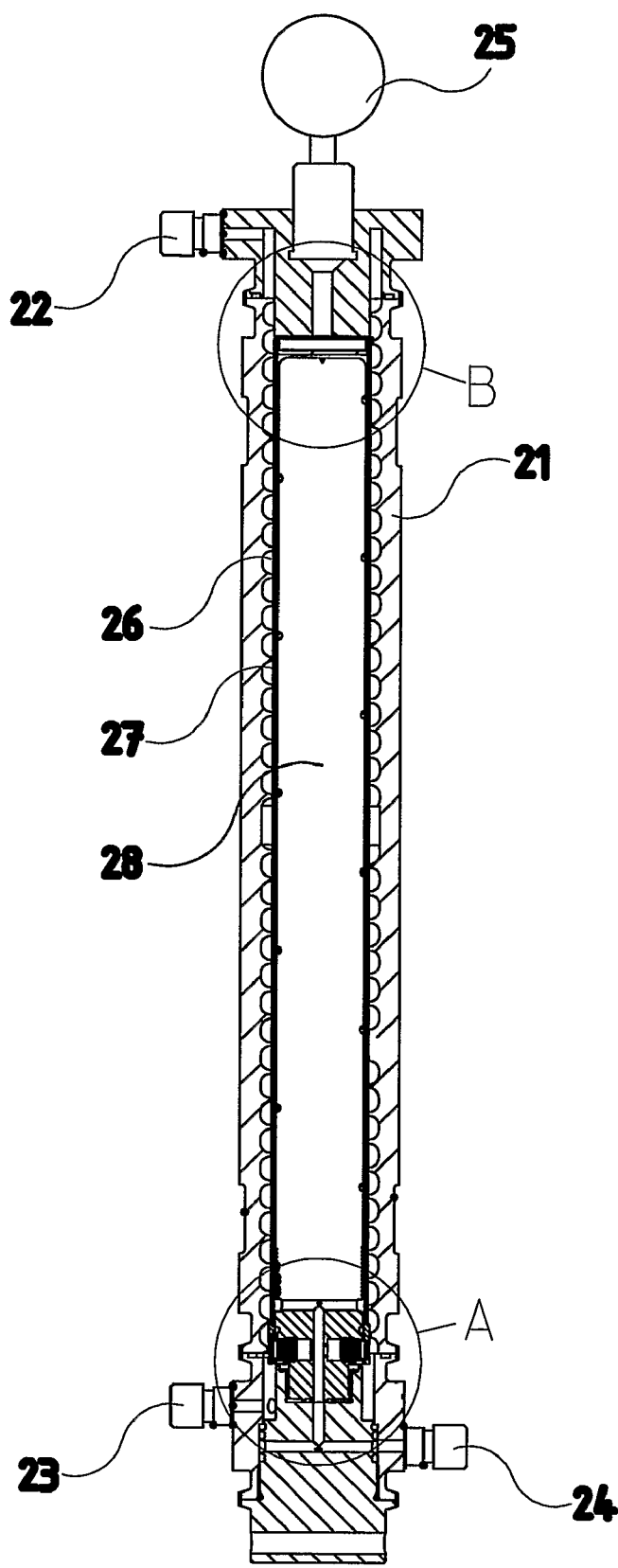
FIG. 2 shows a cross-section view of one preferred embodiment of the filter assembly according to the present invention.

FIG. 2 is a cross sectional view of one embodiment of the filtering apparatus according to the present invention. The apparatus comprises an elongated cylindrical cartridge housing 21, a cylindrical filter cartridge 27, and a solid filler rod 28. The filter cartridge 27 covers the solid filler rod 28 and forms a cavity between its inner surface and the surface of the solid rod 28. The cartridge housing 21 further comprises a cap flange that closes the upper end of the cylindrical housing and a bottom flange that closes the lower end of the housing. The housing determines a slurry input opening 22, a slurry output opening 23, and a filtrate sample out put opening 24. A spiral passageway for the slurry spans between the inner surface of the cartridge housing 21 and the outer surface of the filter cartridge 27. A pressure gauge 25 is arranged to the cartridge housing. A helicoidal groove 26 is worked on the inner surface of the cartridge housing 21. The pitch of the groove is between 8 and 20 mm, preferably it is between 10 and 15 mm. The groove shown in FIG. 2 has a right-hand twist. The downright profile of the groove may have a form of triangle, rectangular or it may be rounded. The profile of the groove shown in FIG. 2 is rounded with a radius of 5 mm. The depth of the groove is adjusted according to the process slurry. The ratio of the inner diameter of the housing to the length of the housing is between 5:100 to 30:100, preferably between 8:100 to 12:100.

Figure 3:
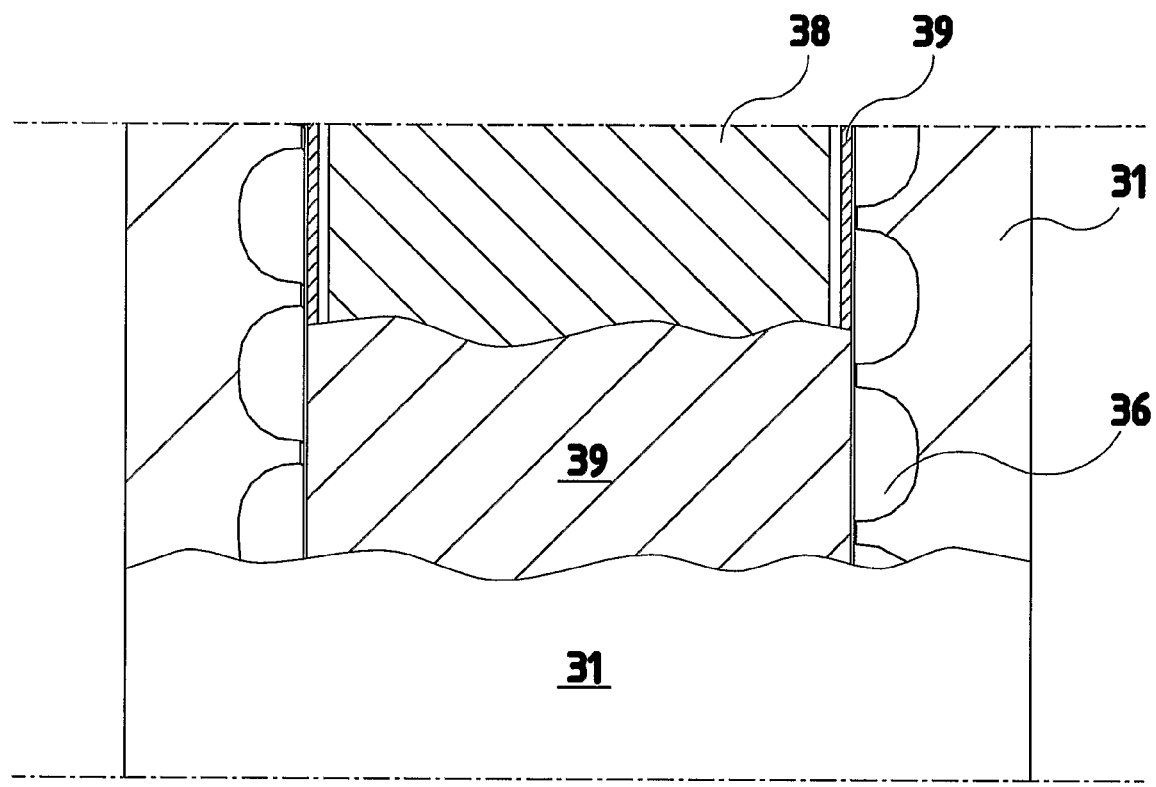
FIG. 3 is detailed cross-section view of the embodiment shown in FIG. 2, and FIG. 4a and FIG. 4b show details A and B respectively of the cross-section view of FIG. 2.

FIG. 3 shows a cut-away view of parts of the filter apparatus according to a preferred embodiment of the present invention. The helicoidal groove 36 is formed on the inside wall of the cartridge housing 31. The surface of the solid filler rod 38 is textured having rifled and grooved surface. The grooves may be longitudinal or radial or both. The rifles may span from the top to the lower end of the rod forming a spiral passageway for the filtrate. Preferably the texture of the solid filler rod comprises both rifles and grooves. The depth of the texture is essentially smaller than the depth of the helicoidal groove forming the passageway for the slurry. The depth of the grooves or rifles is preferably 0.2-5 mm, most preferably 0.5-2 mm. The textured surface expands the cavity formed between the filter cartridge 39 and the solid filler rod 38 so as to facilitate the flow of the filtrate towards the output port of the filtrate.

Figure 4A:
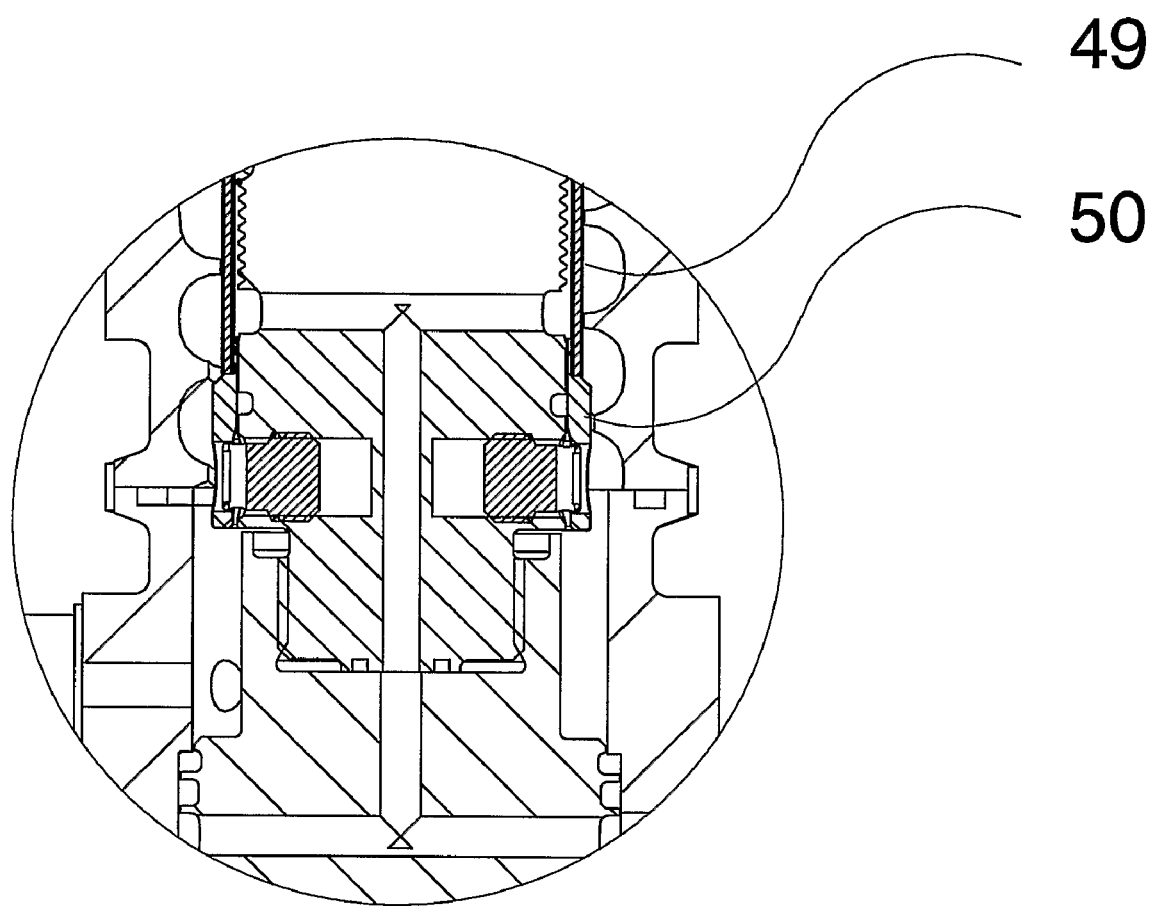
Figure 4B:
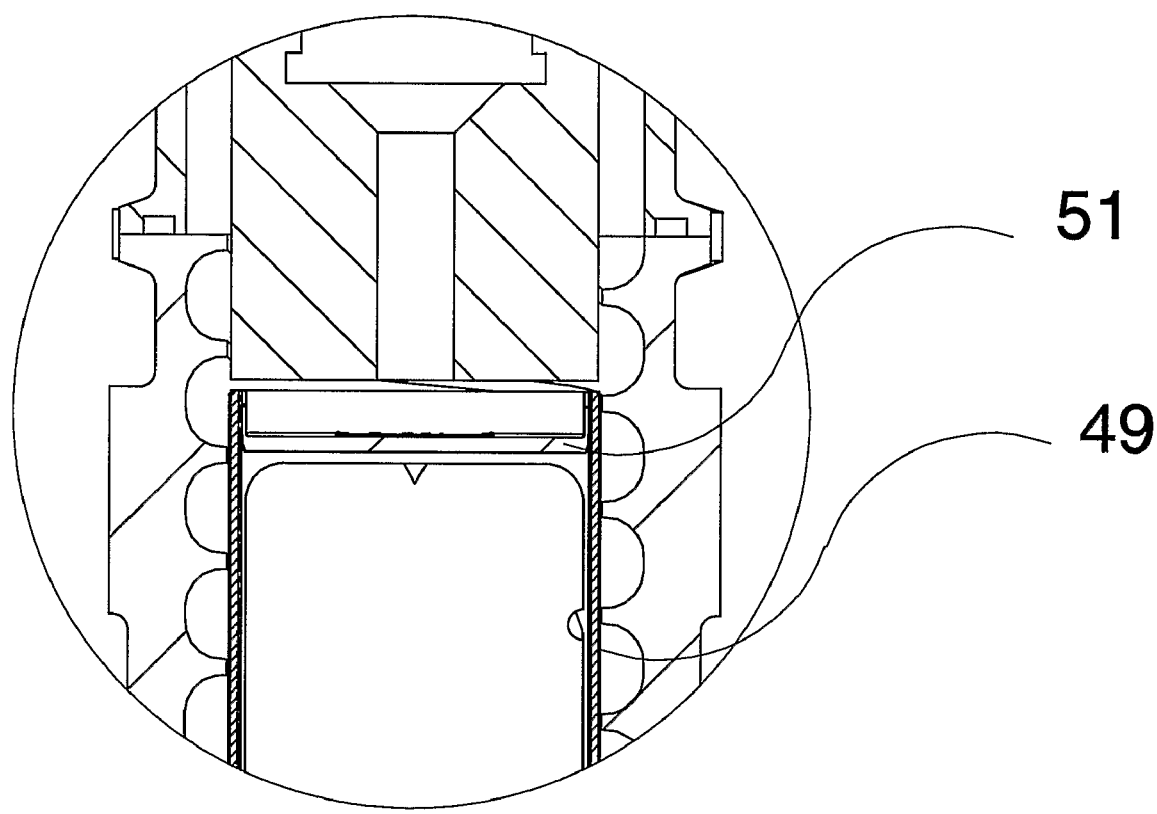

FIG. 4a and FIG. 4b show details A and B of FIG. 2. Filtering-clothe 49 is waterproof arranged to a connection ring 50 and a cap 51. The filtering cloth 49 and the connection ring 50 and the cap 51 comprise preferably same kind of polymer. The filtering cloth 49 and the ring 50 and the cap 51 preferably comprise polyamide or polypropylene.

While the invention has been described with reference to its preferred embodiments, it is to be understood that modifications and variations will occur to those skilled in the art. Such modifications and variations are intended to fall within the scope of the appended claims.

The invention claimed is:

1. An apparatus for forming a solid-free liquid flow from a solid-containing liquid flow, comprising a cartridge housing defining a filtering cavity and inlet and outlet ports for said solid-containing liquid, and a filtering cartridge containing filtering media, and a filtrate output port, wherein the elongated cylindrical cartridge housing defines the filter cavity, the slurry feed port, the slurry outlet port and the a filtrate outlet port, a solid filler rod is arranged to eliminate dead volume of the filter cavity and to support flexible filtering media, a cylindrical filter cartridge comprises said flexible filtering media arranged between the inner surface of the housing and the solid filler rod, a helicoidal passage way for the slurry is defined by the inner surface of the housing and outer surface of the filter cartridge the slurry feed port and the slurry outlet port are both in fluid communication with the helicoidal passage way, and the filtrate outlet port is in fluid communication with an annular cavity defined by the solid filler rod and inner surface of the cylindrical filter cartridge.

2. The apparatus according to claim 1, wherein the helicoidal passageway is determined by the outer surface of the filter cartridge and a worked helicoidal groove on the inner surface of the cartridge housing.

3. The apparatus according to claim 2, wherein the downright profile of the helicoidal groove has a form of triangle, rectangular or it is rounded.

4. The apparatus according to claim 2, wherein the helicoidal groove has a pitch between 8 and 20 mm, preferably between 10 and 15 mm.

5. The apparatus according to claim 1, wherein the ratio of the inner diameter of the housing to the length of the housing is between 5:100 to 30:100, preferably between 8:100 to 12:100.

6. The apparatus according to claim 1, wherein the surface of the solid filler rod is textured to facilitate the flow of the filtrate towards the output port of the filtrate.

7. The apparatus according to claim 6, wherein the surface of the solid filler rod is rifled or grooved or both.

8. The apparatus according to claim 1, wherein the filter cartridge comprises filtering cloth.

9. The apparatus according to claim 8, wherein the filtering cloth comprises polyamide or polypropylene.

10. The apparatus according to claim 1, wherein the filter cartridge comprises filtering cloth that is waterproof arranged to a connection ring and a cap.

11. The apparatus according to claim 10, wherein the filtering cloth, the connection ring and the cap comprise same kind of polymer, such as polyamide or polypropylene.

12. An installation for separating a solid-free liquid flow from a solid-containing process stream comprising means for withdrawing a side stream from the process stream and means for conducting said side stream to a filtering apparatus of claim 1 for separating a solid-free flow from the side stream.

* * * * *